United States Patent [19]

Fidler et al.

[11] Patent Number: 4,916,118

[45] Date of Patent: Apr. 10, 1990

[54] PHARMACEUTICAL ADMINISTRATION SYSTEMS CONTAINING CHEMOTACTIC PEPTIDES

[75] Inventors: Isaiah J. Fidler, Kingwood; Kiyoshi Morikawa; Rajiv Nayar, both of Houston, all of Tex.

[73] Assignee: Board of Regents, The University of Texas System, Austin, Tex.

[21] Appl. No.: 84,636

[22] Filed: Aug. 12, 1987

Related U.S. Application Data

[63] Continuation-in-part of Ser. No. 897,250, Aug. 18, 1986.

[51] Int. Cl.⁴ .................... A61K 37/02; C07K 7/09
[52] U.S. Cl. ........................................ 514/16; 530/328; 530/329
[58] Field of Search .................. 530/324, 328, 329; 514/8, 16

[56] References Cited

U.S. PATENT DOCUMENTS

| | | | |
|---|---|---|---|
| 4,275,000 | 6/1981 | Ross | 530/359 |
| 4,323,560 | 4/1986 | Baschang et al. | 424/88 |
| 4,406,890 | 9/1983 | Tarcsay et al. | 586/53 |
| 4,409,209 | 10/1983 | Baschang et al. | 514/8 |
| 4,480,041 | 10/1984 | Myles et al. | 435/7 |
| 4,612,007 | 9/1986 | Edelson | 604/5 |
| 4,613,322 | 9/1986 | Edelson | 604/6 |
| 4,619,913 | 10/1986 | Luck et al. | 424/131 |
| 4,643,988 | 2/1987 | Segrest et al. | 530/324 |
| 4,683,889 | 8/1987 | Edelson | 604/6 |

Primary Examiner—Delbert R. Philips
Attorney, Agent, or Firm—Mathews, Woodbridge & Collins

[57] ABSTRACT

The present invention relates to pharmaceutical administration systems containing phosphatidylserine and phosphatidylcholine or phosphatidylethanolamine derivatives in the form of liposomes which encapsulate chemotactic peptides such as N-formyl-L-methionyl-L-leucyl-L-phenylalanine. The liposomes are prepared by conventional dispersion methods. The pharmaceutical administration systems when applied in the form of liposomes stimulate macrophage activity which is especially useful in the cancer therapy for combating metastatic tumor cells and for treatment of chronic infections.

9 Claims, No Drawings

PHARMACEUTICAL ADMINISTRATION SYSTEMS CONTAINING CHEMOTACTIC PEPTIDES

CROSS-REFERENCE TO RELATED APPLICATIONS

This is a continuation-in-part of Ser. No. 897,250 filed Aug. 18, 1986, now abandoned.

The present invention relates to pharmaceutical administration systems consisting of chemotactic peptides and phospholipids, a process for the preparation of these administration systems and their method of use.

| List of Abbreviations | |
|---|---|
| FMLP | N-formyl-L-methionyl-L-leucyl-L-phenylalanine |
| ULV | Unilamellar liposomes (vesicles) |
| MLV | Multilamellar liposomes |
| PC | Phosphatidylcholine |
| PS | Phosphatidylserine |
| S.D. | Standard deviation |
| CMEM | Complete minimum essential medium |
| [$^{125}$I]IdUrd | [$^{125}$I]iododeoxyuridine |
| HBSS | Hank's balanced salt solution |
| cpm | counts per minute |
| dpm | disintegrations per minute |
| NEN | New England Nuclear |
| FCS | Fetal Calf Serum |

Recently, synthetic oligopeptides similar to those produced by prokaryotic cells (i.e. bacteria, viruses, and mycobacteria) have been shown to be potent stimulants of macrophages and neutrophil function (Rossman et al., Am. Rev. Respir. Dis. 126 (1982) 136). In vitro studies have shown that synthetic formyl peptides, in particular FMLP, stimulate cell aggregation, chemotaxis, lysosomal enzyme secretion, and extracellular release of oxygen radicals of these cell types. In addition, other cellular functions related to motility (e.g. adherence and spreading) are stimulated when the cells are incubated with these N-formyl peptides.

Liposomes have been described in the literature in numerous publications. Their structure and use have been made the subject of intensive research work. Depending on their shell structure, a distinction is made between unilamellar liposomes or vesicles (ULV) and multilamellar liposomes or vesicles (MLV). In some publications, the term "vesicle" strictly applies to unilamellar liposomes. ULV have a spherical shell consisting of one double layer of lipids, especially phospholipids, whereas MLV have a spherical shell consisting of several double layers arranged in an onionshell-like pattern.

The spherical shell may consist of phospholipids such as phosphatidycholine, phosphatidylethanolamine or phosphatidic acid and optionally "neutral" lipids such as cholesterol. This shell encapsulates an internal volume containing the aqueous phase and the pharmacologically active compound(s).

Depending upon their degree of lipophility and other parameters, such as temperature or concentration, the encapsulated compounds are present in the enclosed aqueous phase and/or in the double layer(s).

There exists a great deal of interest in the therapeutic or diagnostic use of liposomes as carriers of active ingredients of widely varied kinds. Accordingly, liposomes have been proposed as carriers for proteins, for example antibodies, or enzymes, hormones, immunomodulators, vitamins, or, for analytical purposes, as carriers for compounds labelled by radioactive isotopes. For example, in the U.S. Pat. No. 3,993,754 a chemotherapeutic process is disclosed which is useful for the treatment of tumor cells by using liposomes as carriers.

Pharmaceutical administration systems based on liposomes have been described in the general review issued by G. Gregoriadis, Liposome Technology, Vol. II, Incorporation of Drugs, Proteins and Genetic Material, CRC Press 1984. Such systems have the advantage that biologically active material can be introduced into tissues by phagocytosis, especially into tissues of the reticulo-endothelial system. For example, a transport mechanism is known by which antibiotics are introduced into infected tissues by phagocytosis thus causing the accelerated removal or destruction of the infecting microorganism. Endocytosis also is a helpful mechanism in the combat of centres of inflammation. Antirheumatic pharmaceuticals encapsulated in liposomes are preferably introduced into infected tissues. Moreover, cytostatic agents can be introduced into specific organs of the reticulo-endothelial system (liver, spleen or marrow). Additionally, due to filtration in the capillaries of the lung and subsequent transport by migrating monocytes, biologically active material, for example compounds having immunomodulatory properties, can be concentrated in alveolar macrophages. This results in an improved action on metastatic lung tumors and in a simultaneous reduction of toxicity.

Macrophage-mediated destruction of tumors may be enhanced by localization of these effector cells at a tumor site. Augmentation of the infiltration of tumors by macrophages could be achieved if a chemotactic factor were concentrated in the vicinity of the tumor. This could be achieved either by administration of covalently linked conjugates of the chemotactic factor and antibodies reactive with tumor surface antigens (Obrist, R. and Sandberg, R., Cell. Immunol. 81 (1983) 169) or by delivering the chemotactic factors in effector cells, which upon location at a tumor site might release the factor into the medium.

Object of the present invention are pharmaceutical administration systems whose components, when applied in the form of liposomes, are being enriched or concentrated in the lung and/or liver followed by endocytosis of the macrophages and, therefore, activate blood monocytes and thereby macrophages, for example alveolar or peritoneal macrophages. It has been found that aqueous dispersions containing liposomes consisting of phospholipids and encapsulated chemotactic peptides improve the activation of macrophages as compared to aqueous solutions containing unencapsulated chemotactic peptides.

The present invention relates to pharmaceutical administration systems consisting of (a) a phospholipid of the formula

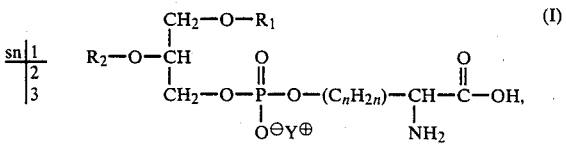

wherein n is one, two or three, $R_1$ and $R_2$ independently of each other represent alkyl, alkenyl or acyl each having 10–20 carbon atoms, and $Y^\oplus$ is the cation of a pharmaceutically acceptable base, (b) a phospholipid of the formula

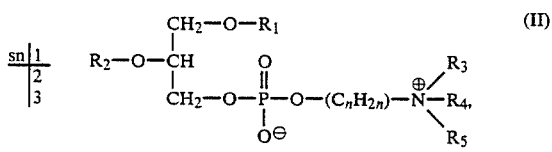

wherein n is two, three or four, $R_1$ and $R_2$ are defined as above and $R_3$, $R_4$ and $R_5$ represent hydrogen or $C_1$–$C_4$-alkyl, (c) a chemotactic peptide or a chemotactic peptide combined with pharmaceuticals selected from the group consisting of antiphlogistics, antibiotics, antileishmaniasis agents, antimycotics, antineoplastics and immunomodulators and, optionally, a pharmaceutically acceptable carrier solution buffered to pH 7.0–7.8 and/or, optionally, pharmaceutically acceptable additives.

In the context of the description of the present invention, the general terms employed hereinbefore and hereinafter preferably have the following meanings:

The term "lower" used in connection with organic radicals, for example lower alkyl, lower alkylene, lower alkoxy, lower alkanoyl, etc., means that such organic radicals, unless expressly defined otherwise, contain up to 7, preferably up to 4, carbon atoms.

The nomenclature of the phospholipids of the formulae I and II is in agreement with the recommendations of the IUPAC and IUB Commission on Biochemical Nomenclature (CBN) according to the Eur. J. of Biochem. 79, 11–21 (1977) "Nomenclature of Lipids" (sn-nomenclature, stereospecific numbering).

In a phospholipid of the formula I (component (a)) the group —$(C_nH_{2n})$— is straight chained or branched alkylene, for example 1,1- or 1,2-ethylene, 1,1-, 1,2- or 1,3-propylene or, preferably, methylene (n=1).

Alkyl $R_1$ and $R_2$ is preferably straight-chained with an even number from 10 to 20 carbon atoms, for example n-decyl, n-dodecyl, n-tetradecyl, n-hexadecyl, n-octadecyl or n-icosyl.

Alkenyl $R_1$ and $R_2$ is preferably straight-chained with an even number form 12 to 20 carbon atoms and one double bond, for example 9-cis-dodecenyl, 9-cis-tetradecenyl, 9-cis-hexadecenyl, 6-cis-, 6-trans-, 9-cis- or 9-transoctadecenyl or 9-cis-icosenyl.

Acyl $R_1$ and $R_2$ is preferably straight-chained with an even number of 10–20 carbon atoms, for example $C_{10}$–$C_{20}$-alkanoyl or $C_{10}$–$C_{20}$-alkenoyl having one double bond.

Alkanoyl $R_1$ and $R_2$ is preferably n-decanoyl, n-dodecanoyl, n-tetradecanoyl, n-hexadecanoyl, n-octadecanoyl and n-icosanoyl.

Alkenoyl $R_1$ and $R_2$ is preferably 9-cis-dodecenoyl, 9-cis-tetradecenoyl, 9-cis-hexadecenoyl, 6-cis-, 6-trans-, 9-cis- or 9-transoctadecenoyl, 11-cis-octadecenoyl and 9-cis-icosenoyl.

The cation $Y^\oplus$ of a pharmaceutically acceptable base is, for example, an alkali metal ion, e.g. the lithium, sodium or the potassium ion, the ammonium ion, a mono-, di- or tri-$C_1$–$C_4$-alkylammonium ion, for example the trimethyl-, ethyl-, diethyl-, or triethylammoniumion, a 2-hydroxyethyl-tri-$C_1$–$C_4$-alkylammoniumion, e.g. the cholinyl or the 2hydroxyethylammonium ion, or the cation of a basic amino acid, for example lysine or arginine.

Preferred are phospholipids of the formula I isolated from natural sources wherein $R_1$ and $R_2$ are different or identical $C_{10}$–$C_{20}$-alkanoyl or $C_{10}$–$C_{20}$-alkenoyl groups, for example n-dodecanoyl, n-tetradecanoyl, n-hexadecanoyl, or n-octadecanoyl, or 9-cis-dodecenoyl, 9-cis-tetradecenoyl, 9-cis-hexadecenoyl, 6-cis-, 6-trans-, 9-cis-, 9-trans- or 11-cis-octadecenoyl or 9-cis-icosenoyl, for example phosphatidylserine from bovine brain, and synthetic phospholipids of the formula I wherein $R_1$ and $R_2$ are identical $C_{10}$–$C_{20}$-alkenoyl groups, for example 9-cis-hexadecenoyl, 6-cis-, 6-trans-, 9-cis-, 9-trans- or 11-cis-octadencenoyl, for example sodium-1,2-di-(9-cis-octadecenoyl)-3-sn-phosphatidyl-(S)-serine.

In a phospholipid of the formula II (component (b)) the group —$(C_nH_{2n})$— is straight chain or branched alkylene, for example 1,1-, 1,2- or 1,3-propylene or 1,2-, 1,3- or 1,4-butylene or, preferably, 1,2-ethylene (n=2).

In a phospholipid of the formula II the groups $R_1$ and $R_2$ have the same definitions as $R_1$ and $R_2$ in the phospholipid of the formula I. The groups $R_3$, $R_4$ and $R_5$ preferably are hydrogen (cephalins) or methyl (lecithins).

Preferred are phospholipids of the formula II, wherein $R_4$, $R_5$ and $R_6$ are hydrogen or methyl, isolated from natural sources from plants or from animals, and wherein $R_1$ and $R_2$ are different or identical $C_{10}$–$C_{20}$-alkanoyl or $C_{10}$–$C_{20}$-alkenoyl groups, for example n-dodecanoyl, n-tetradecanoyl, n-hexadecanoyl, or n-octadecanoyl, or 9-cis-dodecenoyl, 9-cis-tetradecenoyl, 9-cis-hexadecenoyl, 6-cis-, 6-trans-, 9-cis-, 9-trans- or 11-cis-octadecenoyl, or 9-cis-icosenoyl, for example lecithin or cephalin from chicken eggs or soy bean lecithin, synthetic phospholipids (II) wherein $R_1$ and $R_2$ are identical $C_{10}$–$C_{20}$-alkanoyl groups as mentioned above, and synthetic phospholipids (II), wherein $R_1$ is $C_{10}$–$C_{20}$-alkanoyl, for example n-dodecanoyl, n-tetradecanoyl, n-hexadecanoyl, or n-octadecanoyl, and $R_2$ is $C_{10}$–$C_{20}$-alkenoyl, for example 9-cis-hexadecenoyl, 6-cis-, 6-trans-, 9-cis-, 9-trans- or 11-cis-octadecenoyl, especially 1-n-hexadecanoyl-2-(9-cis-octadecenoyl)-3-sn-phosphatidycholine.

The phospholipids comprised in the pharmaceutical administration system of the present invention are dispersed in aqueous phase in the form of liposomes.

Chemotactic peptides are, for example, tri- to decapeptides wherein the terminal amino group has been substituted with a tert-butoxy-carbonyl (BOC) group such as BOC-Met-Leu-Phe-OH, BOC-Nleu-Phe-OH, or BOC-Phe-Leu-Phe-Leu-Phe-OH or are di- to decapeptides wherein the N-terminal group has been substituted with a formyl group such as CHO-Ala-Gly-Ser-Glu-OH, CHO-Met-Ala-OH, CHO-Met-Leu-Tyr-OH, CHO-Met-Met-Met-OH, CHO-Met-Phe-OH, CHO-Met-Phe-Met-OH, CHO-Met-Tyr-OH, CHO-Met-Val-OH, CHO-Nleu-Leu-Phe-OH (Nleu=norleucine), CHO-Nleu-leu-Nleu-Tyr-Lys-OH, CHO-Nleu-leu-Phe-Tyr-OH, CHO-Nleu-leu-Phe-(iodo)Tyr-OH, CHO-Ala-Leu-Phe-OH, CHO-Val-Leu-Phe-OH or CHO-Cyl-Leu-Phe-OH (Cyl=cycloleucine), CHO-Val-Leu-Phe-OH, CHO-Nleu-Leu-Phe-Nleu-Tyr-LysOH, or CHO-Met-Phe-OH(FMP).

Preferred are chemotactic tri- to decapeptides wherein the terminal amino group has been substituted with a formyl group and wherein the primary sequence is Met-Leu-Phe such as CHO-Met-Leu-Phe-methylester, CHO-Met-Leu-Phe-benzamide, CHO-Met-Leu-Phe-benzylester, CHO-Met-Leu-Phe-OH, or CHO-Met-Leu-Phe-Lys-OH.

Most preferred is CHO-Met-Leu-Phe-OH (FMLP).

The chemotactic peptides are administered in the form of liposomes. The liposomes encapsulate these peptides or encapsulate the chemotactic peptides in combination with pharmaceuticals selected from the group consisting of antiphlogistics, antibiotics, antileishmanials, antimycotics, antineoplastics and immunomodulators.

Pharmaceuticals from the group comprising antiphlogistics are, for example, glucocorticoids, for example cortisone, hydrocortisone, prednisone, prednisolone, fluorcortolone, triamcinolone, methylprednisolone, prednylidene, paramethasone, dexamethasone, betamethasone, beclomethasone, fluprednylidene, desoxymethasone, fluocinolone, flumethasone, diflucortolone, clocortolone, clobetasol or fluocortin butyl ester, non-steroidal inflammation-inhibitors (NSAID) from the group comprising substituted phenylacetic acid salts or 2phenylpropionic acid salts, for example alclofenac, ibufenac, ibuprofen, clindanac, fenclorac, ketoprofen, fenoprofen, indoprofen, fenclofenac, diclofenac, flurbiprofen, pirprofen, naproxen, benoxaprofen, carprofen or cicloprofen, anthranilic acid derivatives, for example of the formula

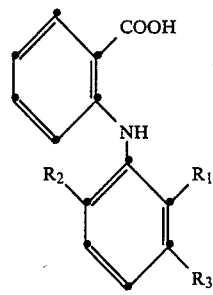

(III)

in which $R_1$, $R_2$ and $R_3$ each represents, independently of one another, hydrogen, methyl, chlorine or trifluoromethyl, for example mefenamic acid, flufenamic acid, tolfenamic acid or meclofenamic acid, anilino-substituted nicotinic acid derivatives, for example miflumic acid, clonixin or flunixin, heteroarylacetic acids wherein heteroaryl is a 2-indol-3-yl or pyrrol-2-yl group, for example indomethacin, oxmetacin, intrazol, acemetazin, cinmetacin, zomepirac, tolmetin, colpirac or tiaprofenic acid, and idenylacetic acid of the sulindac type and analgesically active heteroaryloxyacetic acids, for example benzadac.

Pharmaceuticals from the group comprising antibiotics are, for example, tetracycline antibiotics of the formula

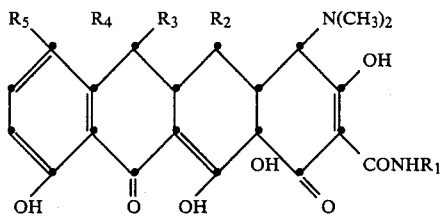

(V)

in which $R_1$ represents hydrogen or pyrrolidin-1-ylmethyl, $R_2$ represents hydrogen or hydroxy, $R_3$ represents hydrogen, hydroxy or methyl, $R_4$ represents hydrogen or methyl and $R_5$ represents hydrogen, chlorine or dimethylamino, for example chlortetracycline, oxytetracycline, tetracycline, demethylchlortetracycline, metacycline, doxycycline, minocycline or rolitetracycline, aminoglycosides, for example kanamycin, amikacin, gentamicin $C_{1a}$, $C_2$, $C_{2b}$ or $C_1$, sisomicin, netilmicin, spectinomycin, streptomycin, tobramycin, neomycin B, dibekacin or kanendomycin, macrolides, for example maridomycin or erythromycin, lincomycins, for example clindamycin or lincomycin, penicillanic acid (6-APA)- and cephalosporanic acid (7-ACA)-derivatives having (6β- or 7β-acylamino groups, respectively, which are present in fermentatively, semi-synthetically or totally synthetically obtainable 6β-acylaminopenicillanic acid or 7β-acylaminocephalosporanic acid derivatives and/or 7β-acylaminocephalosporanic acid derivatives that are modified in the 3-position, for example penicillanic acid derivatives that have become known under the names penicillin G or V, such as phenethicillin, propicillin, nafcillin, oxycillin, cloxacillin, dicloxacillin, flucloxacillin, cyclacillin, epicillin, mecillinam, methicillin, azlocillin, sulbenicillin, ticarcillin, mezlocillin, piperacillin, carindacillin, azidocillin or ciclacillin, or cephalosporin derivatives that have become known under the names cefaclor, cefuroxime, cefazlur, cephacetrile, cefazolin, cephalexin, cefadroxil, cephaloglycin, cefoxitin, cephaloridine, cefsulodin, cefotiam, ceftazidine, cefonicid, cefotaxime, cefmenoxime, ceftizoxime, cephalothin, cephradine, cefamandol, cephanone, cephapirin, cefroxadin, cefatrizine, cefazedone, ceftrixon or ceforanid, and other β-lactam antibiotics of the clavam, penem or carbapenem type, for example moxalactam, clavulanic acid, nocardicine A, sulbactam, aztreonam or thienamycin, and antibiotics of the bicozamycin, novobiocin, chloramphenicol or thiamphenicol, rifampicin, fosfomycin, colistin or vancomycin type.

Pharmaceuticals from the group comprising antileishmaniasis agents are, for example antimony compounds, for example tartar emetic (potassium antimonyl tartrate), stibophen, sodium stibocaptate and sodium stibogluconate.

Pharmaceuticals from the group comprising antimycotics are, for example, thiocarbonic acid derivatives, for example dibenzthione, tolnaftate, or tolciclate, imidazole derivatives, for example clotrimazole, miconazole, econazole, isoconazole or ketoconazole or polyene antibiotics, for example nystatin, natamycin or amphotericin B.

Pharmaceuticals from the group comprising antineoplastics are, for example, alkylating agents having the bis-(2-chloroethyl)-amine group, for example chlormethine, chlorambucil, melphalan, uramustine, mannomustine, estramustine phosphate, mechlorethamine oxide, cyclophosphamide, ifosfamide or trifosfamide, alkylating agents having the aziridine structure, for example tretamine, thiotepa, triaziquone or mitomycin, alkylating methanesulphonic acid esters, for example busulphan, alkylating N-alkyl-N-nitrosourea derivatives, for example carmustine, lomustine, semustine or streptozotocin, and alkylating agents of the mitobronito, dacarbazine or procarbazine type, antimetabolites of the folic acid type, for example methotrexate, purine derivatives, for example mercaptopurine, thioguanine, azathioprine, thiamiprine, vidarabine or puromycin, pyrimidine derivatives, for example fluorouracil, floxuridine, tegafur, cytarabine, idoxuridine, flucytosine, antibiotics that are used in cancer chemotherapy for example dactinomycin, daunorubicin, doxorubicin, mithramycin, bleomycin $A_2$ or $B_2$ or etoposide, and vinca alkaloids, for example vincristine, optionally in combination with chlormethamine, prednisolone or prednisone and procarbazine.

Immunomodulators are, for example, muramyl peptides, for example muramyl dipeptides or muramyl tripeptides, especially of the formula

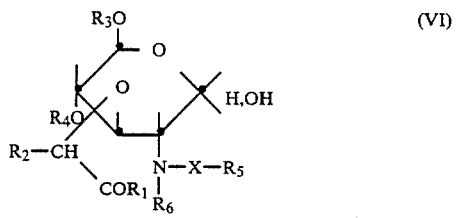

in which X represents the groups —C(=O)— or —C(=O)—O—, $R_1$ represents the L-Ala-D-isoGln-L-Ala-2-(1,2-dipalmitoyl-sn-glycero-3-hydroxy-phosphoryloxy)-ethylamide group, the L-Ala-D-Glu(Cy-L-Ala-2-(1,2-dipalmitoyl-sn-glycero-3-hydroxyphosphoryloxy)-ethylamide) group, the L-Ala-D-isoGlnOH group, the L-Ala-GlnNH$_2$-α-n-butyl ester group, the L-Ala-D-ionGln-L-(stearoyl)-Lys group, the L-Val-D-Gln-NH$_2$-α-n-methyl ester group, the L-Ala-D-isoGln-L-Ala-1,2-dipalmitoyl-sn-glycerine ester group or the L-Ala-D-sioGln-L-Ala-cholesterol ester group, $R_2$ represents hydrogen, methyl or n-propyl, $R_3$ represents hydrogen, n-stearoyl, 10-(2,3-dimethoxy-1,4-dioxo-5-methyl)-2,5-cyclohexadienoyl, 2-behenoyloxy-2-methylpropanoyl or n-octanoyl, $R_4$ represents hydrogen or n-octanoyl, $R_5$ represents $C_1$–$C_4$-alkyl and $R_6$ represents hydrogen or $C_1$–$C_4$-alkyl and the corresponding 2-palmitoylthio derivatives thereof, lipopeptides having immunomodulating properties of the n-lauroyl-L-Ala-D-isoGln-(m-DAP-Gly)-NH$_2$, n-lauroyl-L-Ala-D-isoGln-(L-DAP-Gly)-NH$_2$, n-lauro-yl-L-Ala-D-isoGln-(L-Lys-D-Ala)-NH$_2$, n-octanoyl-L-Ala-D-isoGln-(L-Lys-D-Ala)-NH$_2$ or palmitoyl-Cys-((2R)-2,3-dilauroyloxy-propyl)-Ala-D-Glu-(Gly-taurine-Na)-NH$_2$ type, or they are lymphokines that are secreted by lymphocytes, monocytes or macrophages when these are stimulated by antigens or mitogens or the like.

The group comprising lymphokines includes, for example, known types of interferon, especially natural or recombinant human gamma-interferon, for example human gamma-interferon which can be obtained in accordance with European Patent Application Nos. 63,482, 77,670, 83,777, 88,540, 89,676, 95,350, 99,084, 110,044 and 112,967 and International Application (PCT) Nos. WO 83/04,053 and WO 84/02,129.

Preferred is recombinant human gamma-interferon according to European Patent Application No. 121,157 having the following amino acid sequence:
H$_2$N-Cys-Tyr-Cys-Gln-Asp-Pro-Tyr-Val-Gln-Glu-
Ala-Glu-Asn-Leu-Lys-Lys-Tyr-Phe-Asn-Ala-Gly-
His-Ser-Asp-Val-Ala-Asp-Asn-Gly-Thr-Leu-Phe-
Leu-Gly-Ile-Leu-Lys-Asn-Trp-Lys-Glu-Glu-Ser-
Asp-Arg-Lys-Ile-Met-Gln-Ser-Gln-Ile-Val-Ser-Phe-
Tyr-Phe-Lys-Leu-Phe-Lys-Asn-Phe-Lys-Asp-Asp-
Gln-Ser-Ile-Gln-Lys-Ser-Val-Glu-Thr-Ile-Lys-Glu-
Asp-Met-Asn-Val-Lys-Phe-Phe-Asn-Ser-Asn-Lys-
Lys-Lys-Arg-Asp-Asp-Phe-Glu-Lys-Leu-Thr-Asn-
Tyr-Ser-Val-Thr-Asp-Leu-Asn-Val-Gln-Arg-Lys-
Ala-Ile-His-Glu-Leu-Ile-Gln-Val-Met-Ala-Glu-Leu-
Ser-Pro-Ala-Ala-Lys-Thr-Glu-Lys-Arg-Lys-Arg-
Ser-Gln-Met-Leu-Phe-Gln-Gly-Arg-Arg-Ala-Ser-
Gln-OH, and recombinant human gamma-interferon according to British Patent Application No. 2,107,718 having the following amino acid sequence:
H$_2$N-Cys-Tyr-Cys-Gln-Asp-Pro-Tyr-Val-Lys-Glu-
Ala-Glu-Asn-Leu-Lys-Lys-Tyr-Phe-Asn-Ala-Gly-
His-Ser-Asp-Val-Ala-Asp-Asn-Gly-Thr-Leu-Phe-
Leu-Gly-Ile-Leu-Lys-Asn-Trp-Lys-Glu-Glu-Ser-
Asp-Arg-Lys-Ile-Met-Gln-Ser-Gln-Ile-Val-Ser-Phe-
Tyr-Phe-Lys-Leu-Phe-Lys-Asn-Phe-Lys-Asp-Asp-
Gln-Ser-Ile-Gln-Lys-Ser-Val-Glu-Thr-Ile-Lys-Glu-
Asp-Met-Asn-Val-Lys-Phe-Phe-Asn-Ser-Asn-Lys-
Lys-Lys-Arg-Asp-Asp-Phe-Glu-Lys-Leu-Thr-Asn-
Tyr-Ser-Val-Thr-Asp-Leu-Asn-Val-Gln-Arg-Lys-
Ala-Ile-His-Glu-Leu-Ile-Gln-Val-Met-Ala-Glu-Leu-
Ser-Pro-Ala-Ala-Lys-Thr-Gly-Lys-Arg-Lys-Arg-
Ser-Gln-Met-Leu-Phe-Arg-Gly-Arg-Arg-Ala-Ser-
Gln-OH.

The group comprising lymphokines also includes human interleukin 2 in purified form, for example interleukin 2 which can be obtained in the culture filtrate after activation of human neoplastic leukaemia or lymphoma cells by T-cell mitogens and which is purified by reverse phase HPLC, culture filtrates that can be obtained from cultures having human T-lymphocytes from the spleen or peripheral blood after stimulation by antigens or mitogens, for example human T-cell-leukaemia-lymphoma viruses (HTLV-I), phytohaemagglutinin or concanavalin A, and that contain mixtures that have components which have become known under the terms macrophage migration inhibition factor (MIF), leucocyte migration inhibition factor, leucocyte migration amplification factor, macrophage-activating factor (MAF), colony-stimulating factor, interleukin 1 and 2 and gamma-interferon, especially those culture filtrates or isolates having a high content of macrophage-activating factor (MAF).

The pharmaceutical administration systems according to the present invention, when applied in the form of liposomes, are characterised by their excellent macrophage stimulating activity and in general by their excellent pharmakokinetic profile.

Thus, very rapid endocytosis takes place, especially through the cells of the monocytic system. Liposomes that encapsulate the above-mentioned chemotactic peptides as inclusion compounds can be enriched particularly well in the lung and liver and are subjected to rapid endocytosis by macrophages. In particular, alveolar macrophages are stimulated and physiologically abnormal materials, for example viruses or proliferating tumor cells, are eliminated. The pharmaceutical compositions according to the invention, whenever administered in the form of liposomes, therefore, are especially suitable in cancer chemotherapy for combating tumor metastasis.

Lipsomes containing chemotactic peptides in combination with antiinflammatory drugs, antibiotics, antileishmanial agents, antimycotics or antineoplastics also deliver these drugs specifically to the site of inflammation, infection or to tumor cells and, therefore, increase the therapeutic efficacy of these drugs as compared to non-encapsulated drugs.

Aquaous liposome dispersions wherein the phospholipids of the formulae I and II are the encapsulating material and chemotacic peptides especially in combination with other pharmaceuticals, are encapsulated, optionally after concentration or isolation of the liposomes, for example in the utracentrifuge, are suitable for therapeutic purposes for oral (p.o.) or especially parenteral (buccal, lingual, sublingual, i.v., i.c., epicutane, s.c., i.m. or nasal) administration.

For oral administration, the liposome-containing aqueous dispersion can be mixed with pharmaceutically acceptable diluents or carriers, or with customary additives, for example colorings or flavorings, or cab be used in the form of a syrup or in the form of capsules.

For parenteral administration (epicutane) the liposome-containing aqueous dispersion is admixed with customary thickeners, for example hydroxypropylcellulose, suitable preservatives, antioxidants and optionally perfumes, and can also be used in the form of a lotion or gel for application to the skin or mucous membranes.

For parenteral administration (i.v., s.c.), the aqueous dispersion of the enriched liposomes is suspended in a suitable carrier liquid, for example sterile, calcium free, isotonic sodium chloride or glucose solution, optionally buffered to pH 7.2–7.4.

Based on the present experimental results it is estimated that the highest dose to be applied to a human of about 70 kg weight is about one gram of liposomes containing 2000 microgramm of the chemotactic peptide, the lowest dose being about 100 mg of liposomes containing 100 microgramm of the chemotactic peptide. The highest and lowest dose of the encapsulated material, the concentration of the phospholipids in the aqueous phase as well as the proportions of the lipid components (I) and (II) can be varied according to results to be established experimentally in clinical trials.

The pharmaceutical administration system according to the present invention may also consist of a "kit of parts" set comprising vials or bottles containing the pharmaceutical components to be encapsulated and the phospholipids (I) and (II).

The present invention preferably relates to pharmaceutical administration systems consisting of (a) A phospholipid of the formula I wherein n, $R_1$, $R_2$ and $Y^\oplus$ are defined as above, (b) a phospholipid of the formula II wherein n and $R_1$ to $R_5$ are defined as above.

(c) N-formyl-L-methionyl-L-leucyl-L-phenylalanine (FMLP) or N-formyl-L-methionyl-L-phenylalanine (FMP), optionally in combination with antiinflammatory agents, antibiotics, antileishmaniasis agents, antimycotics or antineoplastics and, optionally, a pharmaceutically acceptable carrier solution buffered from pH 7.2 to 7.4.

The present invention specifically relates to pharmaceutical administration systems consisting of (a) a phospholipid of the formula I wherein n is one, $R_1$ and $R_2$ are acyl each having 10 to 20 carbon atoms and $Y^\oplus$ is the sodium ion, (b) a phospholipid of the formula II wherein n is two, $R_1$ and $R_2$ are acyl each having 10 to 20 carbon atoms and $R_3$ to $R_5$ represent hydrogen or methyl, (c) FMLP or FMP, optionally in combination with N-acetylmuramyl-L-alanyl-D-isoglutaminyl-L-alanine-2-(1,2-dipalmitoyl-sn-glycero-3-hydroxyphosphoryloxy)-ethylamide, the sodium salt of N-acetyl-desmethylmuramyl-L-alanyl-D-isoglutamine or the sodium salt of N-acetyl-D-muramyl-L-alanyl-D-isoglutamine and, optionally, a pharmaceutically acceptable carrier solution buffered from pH 7.2 to 7.4.

The present invention more specifically relates to pharmaceutical administration systems consisting of (a) synthetic, essentially pure sodium-1,2-di-(9-cis-octadecenoyl)-3-sn-phosphatidyl-(S)-serine (I), (b) synthetic, essentially pure 1-n-hexadecanoyl-2-(9-cis-octadecenoyl)-3-sn-phosphatidylcholine (II), (c) FMLP or FMP, optionally in combination with N-acetylmuramyl-L-alanyl-D-isoglutaminyl-L-alanine-2-(1,2-dipalmitoyl-sn-glycero-3-hydroxyphosphoryloxy)-ethylamide, the sodium salt of N-acetyl-desmethylmuramyl-L-alanyl-D-isoglutamine or the sodium salt of N-acetyl-D-muramyl-L-alanyl-D-isoglutamine and, optionally, a pharmaceutically acceptable carrier solution buffered from pH 7.2 to 7.4.

The pharmaceutical administration systems suitable for application in the form of liposomes are manufactured by standard methods, for example by preparing a homogeneous mixture of the phospholipids of the formulae I and II and component (c) and dispersing the homogeneous mixture obtained in an aqueous phase and, if necessary, buffering the aqueous dispersion to pH 7.0 to 7.8 and, optionally, concentrating and/or separating the liposomes obtained.

The homogeneous mixture is prepared by formation of a film or a lyophilisate of the phospholipids and component (c). The film is prepared by dissolving the phospholipids (I) and (II) and component (c) in an organic solvent and stripping the solvent.

Suitable organic solvents are, for example, unsubstituted or substituted, for example halogenated, aliphatic or cycloaliphatic hydrocarbons, for example n-hexane, cyclohexane, methylenechloride, or chloroform, alcohols, for example methanol or ethanol, lower alkanexcarboxylic acid esters or amides, for example acetc acid ethylester or dimethylformamide, or ethers, for example diethylether, tetrahydrofurane or dioxane, or mixtures of these solvents.

The organic solvent is subsequently stripped by applying reduced pressure, or by blowing off with an inert gas, for example dry nitrogen. The lyophilisate is formed by lyophilizing in a conventional manner a solution of the phospholipids (I) and (II) and component (c) in an organic solvent according to the method as dscribed in the U.S. Pat. No. 4,311,712. Suitable solvents for the preparation of lyophilisates are in the solid state together with the phospholipids (I) and (II) at the temperature of the lyophilisation process and have a melting point of more than 0° C., for example glacial acetic acid, benzene or dioxane, especially tert-butanol.

A homogeneous mixture may also be prepared by spray-drying a solution of the phospholipids (I) and (II) in an organic solvent having a low boiling point such as chloroform. A powder is obtained by this method.

In the homogeneous mixture, the ratio of the phospholipid component (I) to the phospholipid component (II) is approximately 10 v. 90 up to 50 v. 50 mole per cent. Preferred is the ratio 30 v. 70 mole per cent. The approximate ratio of the molar amounts of the encapsulated material divided by the total amount of the phospholipids (I) and (II) is about 0.0001 to 0.1 v. 1.0, preferably 0.005 to 0.01 v. 0.1.

The dispersion method is carried out by adding the homogeneous mixture of the phospholipids (I) and (II) and component (c) to the aqueous phase and by agitation of the aqueous phase (vigorous shaking—Vortex mixer or stirring at high speed). A mixture of small, large, unilamellar or multilamellar liposomes is formed spontaneously at a high rate without supplying external energy. Approximately 0.1 to 40 per cent per weight, preferably 2 to 20 per cent weight, of the homogeneous mixture relative to the total weight of the aqueous dispersion can be dispersed in the aqueous phase. Preferably, such dispersions are further diluted to about 1 micromole lipid per ml. The liposome dispersions of that concentration have entrapped up to approximately 2.5 microliters of the aqueous phase per micromole of the lipid.

The preparation of the pharmaceutical compositions according to the present invention in the form of liposomes can also be carried out by other methods known in the art for preparing liposomes, for example by sonication with ultrasonic waves, by infusion methods or reversed phase evaporation.

The dispersion step is performed at temperatures below 60° C., preferably to room temperature. In view of the potential thermal sensitivity of the encapsulated material, the dispersion may be carried out under cooling and, optionally, under inert gas atmosphere, for example nitrogen or argon atmosphere.

The liposomes obtained can be made storage stable in the aqueous phase up to several weeks or months after addition of stabilizers, for example mannite or lactose.

The phospholipids of the formulae I and II are known. Some of them are commercially available (Avanti, Sigma, Fluka, Serva). The preparation of 1,2-di-(9-cis-octadecenoyl)-3-sn-phosphatidyl-(S)-serine and of analogous lipids has been described by Browing J. and Seelig J. in Chem. and Phys. of Lipids 24 (1979) 103–118.

The chemotactic peptides mentioned above are also known and most of them are commercially available, see e.g. the Sigma Cataloque.

The following examples are illustrating the invention without limiting the scope thereof. Temperatures are given in degrees Celsius (centigrade).

EXAMPLE 1

0.1 mg of N-Formyl-L-methionyl-L-leucyl-L-phenylalanine, 75 mg of (at least 95% pure) sodium 1,2-di-(9-cis-octadecenoyl)-3-sn-phosphatidyl-(S)-serine (manufactured according to Browning J. and Seeling J., Chem. and Physics of Lipids 24 (1979) 103–118) and 175 mg of (at least 95% pure) 1-n-hexadecanoyl-2-(9-cis-octadecenoyl)-3-sn-phosphatidylcholine (Avanti, Polar Lipids) are dissolved in 786 mg sterile tert-Butanol in a round-bottomed flask. The solution is sterile-filtered over Acrodisc ® filter ($2.0 \times 10^{-7}$ m), introduced into a sterile vial and frozen at $-45°$. The vial is dried in vacuo until a temperature of 25° is reached, and sealed unter an argon atmosphere.

Before use, 2.5 ml of sterile, calcium-free, phosphate-buffered (pH 7.2-7.4) saline solution (Dulbecco) are added to this dry preparation (lyophilisate) at room temperature, using a sterile syringe, and the vial is skaken for one minute in a standardised laboratory shaking apparatus (Vortex at dial setting 6). The resulting liposome dispersion is storable at 4° and suitable for parenteral (i.v.) administration.

EXAMPLE 2

Aqueous dispersions containing liposomes consisting of 75 mg (0.091 mmol) of sodium 1,2-di-(9-cis-octadecenoyl)-3-sn-phosphatidyl-(S)-serine, 175 mg (0.231 mmol) of 1-n-hexadecanoyl-2-(9-cisoctadecenoyl)-3-sn-phosphatidyl choline and from more than 0.1 mg up to 10 mg of N-formyl-L-methionyl-L-leucyl-L-phenylalanine can be manufactured in a manner analogous to that described in Example 1.

EXAMPLE 3:

Aqueous dispersions containing liposomes consisting of 75 mg (0.091 mmol) of sodium 1,2-di-(9-cis-octadecenoyl)-3-sn-phosphatidyl-(S)-serine, 175 mg (0.231 mmol) of 1-n-hexadecanoyl-2-(9-cisoctadecenoyl)-3-sn-phosphatidyl choline, 0.1 mg N-formyl-L-methionyl-L-leucyl-L-phenylalanine and 0.1 mg N-acetylmuramyl-L-alanyl-D-isoglutaminyl-L-alanin-2-(1,2-dipalmitoyl-sn-glycero-3-hydroxyphosphoryloxy)-ethylamide (prepared according to European Patent No. 25 495) can be manufactured in a manner analogous to that described in Example 1.

EXAMPLE 4

0.1 mg of N-formyl-L-methionyl-L-leucyl-L-phenylalanine, 75 mg (at least 95% pure) sodium 1,2-di-(9-cis-octadecenoyl)-3-sn-phosphatidyl-(S)-serine (manufactured according to Browning J. and Seeling J., Chem. and Physics of Lipids 24 (1979) 103–118) and 175 mg of (at least 95% pure) 1-n-hexadecanoyl-2-(9-cis-octadecenoyl)-3-sn-phosphatidylcholine (Avanti, Polar Lipids) are dissolved in 786 mg of sterile tert-butanol in a round-bottomed flask. The solution is sterile-filtered over ACRODISC filter ($2.0 \times 10^{-7}$M), introduced into a sterile vial, and frozen at $-45°$. The vial is dried in vacuo until a temperature of 25° is reached and sealed under an argon atmosphere.

Before use, 2.5 ml of sterile recombinant human gamma interferon solution just diluted to $2 \times 10^5$U/ml in sterile calcium-free phosphate buffered saline (pH 7.2-7.4) (Dulbecco) is added to this dry preparation (lyophilisate) at room temperature using a sterile syringe, and the vial is shaken for one minute in a standardized laboratory shaking apparatus (Vortex, at dial setting of 7). The resulting liposome dispersion is suitable for parenteral (i.v.) administration.

EXAMPLE 5: TEST REPORT

I. Materials and Methods

A. Preparation of free FMLP stock solution.

FMLP was purchased from Sigma Chemical Co. The stock solution (10 mM) was made in methanol and stored at $-70°$ before use. For free form use, the stock solution was diluted to concentrations between $10^{-4}$M and $10^{-7}$M with CMEM containing 5% FBS.

B. Preparation of FMLP-liposomes.

To encapsulate FMLP into liposomes, FMLP from the methanol stock solution was admixed in chloroform with phospholipids PC/PS of Example 1, 7:3 molar ratio). The solvent and residual solvent was evaporated under nitrogen for at least 1 hour. Multilamellar vesicles (MLV) were prepared by adding CMEM to the dry film followed by vortex mixing till a homogenous suspension of liposomes was achieved. The free unencapsulated FMLP was removed by pelleting the MLV at 12,000 g for 15 min.

$10^{-3}$M FMLP=Phospholipid:FMLP mol ratio 1:1
$10^{-4}$M FMLP=Phospholipid:FMLP mol ratio 10:1
$10^{-5}$M FMLP=Phospholipid:FMLP mol ratio 100:1
$10^{-6}$M FMLP=Phospholipid:FMLP mol ratio 1000:1
$10^{-4}$M FMLP=Phospholipid:FMLP mol ratio 10000:1

II In-Vitro Assay of Macrophage Mediated Cytotoxicity

Macrophage mediated cytotoxicity was assessed by a radioactive release assay as described in Sone S. and Fidler I. J., Cell Immunology 57, 42 (1981). Target cells in exponential growth phase were incubated for 24 h in medium supplemented with [$^{125}$I]IdUrd (0.2 μCi/ml; specific activity, 200 mCi/mmol; New England Nuclear, Boston, Mass.). The cells then were washed 3 times with warm HBSS to remove unbound radiolabel, harvested by a short trypsinization (0.25% Difco trypsin and 0.02% EDTA for 1 min at 37°), and resuspended in CMEM containing 5% FBS. Viable cells were plated into the wells containing macrophages to achieve a population density of 2500 macrophages and 250 tumor cells per sq mm (or an initial macrophage:target cell ratio of 10/1). At this population density, normal (untreated) macrophages are not cytotoxic to neoplastic cells. No significant differences were detected in the plating efficiency (binding) of [$^{125}$I]IdUrd-labeled target cells to control or liposome-treated macrophage populations. Radiolabeled target cells also were plated alone as an additional control group. The macrophage-target cell cultures were refed with medium 24 h after the addition of the target cells to remove all nonplated cells and then were incubated for up to 3 days at 37°. At this time, the cultures were washed twice with HBSS to remove adherent cells, and the remaining viable, adherent cells were lysed with 0.1 ml of 0.1N NaOH. The lysate was absorbed in a cotton swab and placed directly into 10×75 mm tubes; radioactivity was measured in a gamma counter. Maximal in vitro macrophage-mediated cytotoxicity in this assay was obtained after 3 days of incubation with target cells, and macrophages did not reincorporate [$^{125}$I]IdUrd released from dead target cells. The cytotoxic activity of the macrophages was calculated as follows:

$$\% \text{ Cytotoxicity} = \frac{\begin{array}{c}(\text{cpm in target cells cultured with}\\ \text{normal macrophages}) - \\ (\text{cpm in target cells cultured with}\\ \text{test macrophages})\end{array}}{\text{cpm in target cells cultured}\\ \text{with normal macrophages}} \times 100$$

Experimental results were analyzed for their statistical significance by Student's 2-tailed t test.

As shown in the Table, PC/PS-FMLP MLV at all FMLP concentrations ($10^{-8}$ to $10^{-4}$M) efficiently activated mouse macrophages to lyse target tumor cells during 72 hours of co-cultivation. In contrast, FMLP in free form at all concentrations was ineffective in rendering macrophages tumoricidal. Collectively, these results show that FMLP encapsulated in Liposomes acts as a macrophage activating agent.

TABLE

Effect of FMLP entrapped in PC/PS-FMLP on cytotoxic activity of mouse peritoneal macrophages

| Macrophage Treatment | cpm +/− S.D. (specific cytotoxicity, %) | |
|---|---|---|
| | Expt. I | II |
| Tumor alone | 2326 + 145 | 2300 + 73 |
| Tumor + Mac | 2483 + 83 | 2117 + 187 |
| PC/PS-MLV | 2238 + 3 | 1988 + 341 |
| PC/PS-FMLP ($10^{-8}$ M) | 1784 + 249 (28) | 1103 + 135 (48) |
| PC/PS-FMLP ($10^{-7}$ M) | 1922 + 168 (23) | 1217 + 148 (43) |
| PC/PS-FMLP ($10^{-6}$ M) | 1804 + 57 (28) | 1597 + 258 (25) |
| PC/PS-FMLP ($10^{-5}$ M) | 1804 + 97 (28) | 1198 + 184 (38) |
| PC/PS-FMLP ($10^{-4}$ M) | 1829 + 145 (27) | 1300 + 297 (39) |
| Free FMLP ($10^{-8}$ M) | 2567 + 70 | 2441 + 32 |
| Free FMLP ($10^{-7}$ M) | 2559 + 109 | 2298 + 178 |
| Free FMLP ($10^{-6}$ M) | 2633 + 61 | 2408 + 32 |
| Free FMLP ($10^{-5}$ M) | 2619 + 82 | 2455 + 106 |
| Free FMLP ($10^{-4}$ M) | 2478 + 74 | 2263 + 361 |
| LPS (10 μg/ml) | 1973 + 293 (21) | |

What is claimed is:

1. A composition operable to produce a pharmaceutical administration system in liposome form, said composition comprising:

(a) a first phospholipid of the formula:

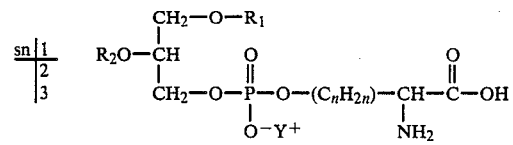

wherein
n is 1, 2, or 3;
each of $R_1$ and $R_2$, independently of the other, is alkyl, alkenyl, or acyl of from 10 to 20 carbon atoms; and
$Y^+$ is the cation of a pharmaceutically acceptable base;

(b) a second phospholipid of the formula:

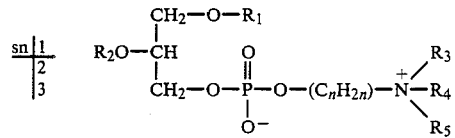

wherein
n is 2, 3, or 4;
each of $R_1$ and $R_2$, independently of the other, is as herein defined; and
each of $R_3$, $R_4$, and $R_5$, independently of the other, is hydrogen or alkyl of 1 to 4 carbon atoms, said second phospholipid being present with respect to said first phospholipid in a mole percent ratio of from about 9:1 to about 1:1; and (c) at least one chemotactic peptide having pharmacological activity, the ratio of the molar amount of said chemotactic peptide to the total molar amount of said first and second phospholipids of being from about 0.0001:1 to about 0.1:1.

2. A composition according to claim 1 including a pharmaceutically acceptable carrier solution, the pH of which is buffered to from 7.0 to 7.8.

3. A composition according to claim 1 wherein said chemotactic peptide is combined with at least one member selected from the group consisting of an antiinflammatory agent, an antibiotic, an antileishmaniasis agent, an antimycotic agent, and an antineoplastic agent.

4. A composition according to claim 3 including a pharmaceutically acceptable carrier solution, the pH of which is buffered to from 7.0 to 7.8.

5. A composition according to claim 2 wherein in said first phospholipid, n is 1, each of $R_1$ and $R_2$, independently of the other, is alkyl of 10 to 20 carbon atoms, and $Y^+$ is the sodium cation;

in said second phospholipid, n is 1, each of $R_1$ and $R_2$, independently of the other, is alkyl of 10 to 20 carbon atoms, and each of $R_3$ and $R_4$, independently of the other, is hydrogen or methyl; and the ratio of the molar amount of said chemotactic peptide to the total molar amount of said first and second phospholipids is from about 0.0005:1 to about 0.001:1.

6. A composition according to claim 5 wherein said chemotactic peptide is N-formyl-L-methionyl-L-leucyl-L-phenylalanine or N-formyl-L-methionyl-L-phenylalanine.

7. A composition according to claim 5 wherein said first phospholipid is sodium 1,2-di-(9-cis-octadecenoyl)-3-sn-phosphatidyl-(S)-serine and said second phospholipid is 1-n-hexadecanoyl-2-(9-cis-octadecenoyl)-3-sn-phosphatidylchloine.

8. A composition according to claim 7 wherein said chemotactic peptide is N-formyl-L-methionyl-L-leucyl-L-phenylalanine or n-formyl-L-methionyl-L-phenylalanine.

9. A composition according to claim 8 wherein said N-formyl-L-methionyl-L-leucyl-L-phenylalanine or N-formyl-L-methionyl-L-phenylalanine is combined with at least one member selected from the group consisting of N-acetylmuramyl-L-alanyl-D-isoglutaminyl-L-alanine-2-(1,2-dipalmitoyl-sn-glycero-3-hydroxyphosphory)-ethylamide, the sodium salt of N-acetyldesmethylmuramyl-L-alanyl-D-isoglutamine, and the sodium salt of N-acetyl-D-muramyl-L-alanyl-D-isoglutamine.

* * * * *